(12) United States Patent
Koenig

(10) Patent No.: US 11,680,932 B2
(45) Date of Patent: Jun. 20, 2023

(54) METHOD AND APPARATUS FOR OPERATING A MULTI-GAS SENSOR

(71) Applicant: TDK CORPORATION, Tokyo (JP)

(72) Inventor: Matthias Koenig, Munich (DE)

(73) Assignee: TDK Corporation, Tokyo (JP)

( * ) Notice: Subject to any disclaimer, the term of this patent is extended or adjusted under 35 U.S.C. 154(b) by 440 days.

(21) Appl. No.: 16/878,167

(22) Filed: May 19, 2020

(65) Prior Publication Data
US 2020/0371076 A1 Nov. 26, 2020

(30) Foreign Application Priority Data
May 21, 2019 (DE) .......................... 102019113539.7

(51) Int. Cl.
*G01N 33/00* (2006.01)
*G01N 27/416* (2006.01)

(52) U.S. Cl.
CPC ..... *G01N 33/0006* (2013.01); *G01N 27/4163* (2013.01)

(58) Field of Classification Search
CPC .. G01N 33/00; G01N 27/416; G01N 33/0006; G01N 27/4163
USPC .......................................................... 73/1.06
See application file for complete search history.

(56) References Cited

U.S. PATENT DOCUMENTS

| | | | |
|---|---|---|---|
| 5,675,070 A * | 10/1997 | Gelperin | G01N 33/0031 73/23.34 |
| 7,000,463 B1 | 2/2006 | Shajii et al. | |
| 7,937,984 B2 * | 5/2011 | Tobias | G01N 33/0006 73/1.06 |
| 10,221,671 B1 * | 3/2019 | Zhang | G06N 3/084 |

(Continued)

FOREIGN PATENT DOCUMENTS

| | | |
|---|---|---|
| DE | 19628033 C1 | 11/1997 |
| DE | 112005002773 T5 | 10/2007 |
| EP | 2738555 B1 | 12/2014 |

OTHER PUBLICATIONS

Deepak, P., et al., "Arlilicial Neural Network for Automated Gas Sensor Calibration," International Journal of Advanced Computational Engineering and Networking, ISSN: 2320-2106, vol. 4, Issue 9, Sep. 2016, pp. 69-71.

*Primary Examiner* — Peter J Macchiarolo
*Assistant Examiner* — Mohammed E Keramet-Amircolai
(74) *Attorney, Agent, or Firm* — Slater Matsil, LLP

(57) ABSTRACT

A method and apparatus for operating a multi-gas sensor are disclosed. In an embodiment, a method includes providing at least one calibration input comprising sensor design data of the multi-gas sensor, which varies dependent on production process parameters, and/or sensor production process parameter data of the multi-gas sensor, and/or measurement results of the multi-gas sensor captured when the multi-gas sensor is exposed to one of the gases or a gas mixture to be detected and/or sensed by the multi-gas sensor; providing a trained neural network including an input layer with K input (Continued)

nodes, an output layer with L output nodes and at least one hidden layer; storing each calibration input as a fixed input to a corresponding input node of the trained neural network; and providing a multi-gas sensor output for at least a part of the gases to be detected and/or sensed by the multi-gas sensor dependent on the trained neural network and actual measured sensor values from the sensor elements.

8 Claims, 3 Drawing Sheets

(56) References Cited

U.S. PATENT DOCUMENTS

| | | | | |
|---|---|---|---|---|
| 2008/0067066 | A1* | 3/2008 | Okumura | G01N 27/4077 204/424 |
| 2011/0048970 | A1* | 3/2011 | Sugaya | G01N 27/419 205/781 |
| 2011/0259084 | A1* | 10/2011 | Atsumi | G01N 27/4067 73/31.05 |
| 2012/0043205 | A1* | 2/2012 | Matsuoka | G01N 27/407 204/410 |
| 2013/0167622 | A1* | 7/2013 | Frivik | F01N 3/208 73/61.61 |
| 2013/0174646 | A1* | 7/2013 | Martin | F24F 11/62 73/31.02 |
| 2013/0269411 | A1* | 10/2013 | Selman | G01N 33/2823 95/266 |
| 2013/0291662 | A1* | 11/2013 | Johnson | G01N 27/4145 73/866 |
| 2015/0020615 | A1* | 1/2015 | Gettings | G08B 21/18 73/865.8 |
| 2015/0323511 | A1* | 11/2015 | Hendry | A61B 5/1495 73/1.02 |
| 2017/0356869 | A1* | 12/2017 | Koenig | G01N 27/121 |

* cited by examiner

METHOD AND APPARATUS FOR OPERATING A MULTI-GAS SENSOR

CROSS-REFERENCE TO RELATED APPLICATIONS

This application claims priority of German Patent Application No. 102019113539.7, filed on May 21, 2019, which application is hereby incorporated herein by reference.

TECHNICAL FIELD

The present invention relates to a method and an apparatus for operating a multi-gas sensor. Furthermore, the present invention relates to a computer program and a computer program product. Additionally the present invention relates to a multi-gas sensor.

BACKGROUND

More and more sensors are being used in smartphones. Most of them have a human counterpart:

Eyes <-> camera, ears <-> microphone, sense of touch <-> touchscreen, sense of balance <-> gyroscope etc.

What is still missing is the sense of smelling. Recently new miniaturized gas sensors capable of detecting different gases have been introduced, which are cheap and small. In many applications it is sufficient to just measure one gas. But from an application perspective it is much more interesting to detect more than one gas. There are many different ways of building such a multi-gas sensor. However, the gas sensors need to be calibrated to the different test gases. This means that every produced gas sensor needs to be exposed to the desired test gases and its electrical behaviour needs to be measured. With this data it is then possible to calibrate the multi-gas sensor. Unfortunately it takes very long to test gas sensors as gas exchanges take a lot of time. If a gas sensor is to be calibrated to many different gases, the calibration time will get longer and longer with each additional gas.

SUMMARY

Embodiments provide a method and an apparatus for operating a multi-gas sensor allowing for a cost-effective deployment of the multi-gas sensor while at the same time ensuring a sufficient measuring accuracy of the multi-gas sensor.

Embodiments are distinguished by a method and a corresponding apparatus for operating a multi-gas sensor, wherein the multi-gas sensor comprises multiple sensor elements. The multi-gas sensor is configured to detect and/or sense a predefined number M of different gases. For operating the multi-gas sensor at least one calibration information is provided. The at least one calibration information comprises sensor design data of the multi-gas sensor which varies dependent on production process parameters and/or sensor production process parameter data of the multi-gas sensor and/or measurement results of the multi-gas sensor captured when the multi-gas sensor is exposed to one of the gases or a gas mixture to be detected and/or sensed by the multi-gas sensor. Furthermore a trained neural network is provided. The trained neural network comprises an input layer with K input nodes, an output layer with L output nodes and at least one hidden layer, wherein L, M and K are natural numbers.

Preferably, the number L output nodes is equal to the number M of different gases the multi-gas sensor is configured to detect and/or sense. Preferably, the number K of input nodes is greater than the number M of different gases the multi-gas sensor is configured to detect and/or sense M.

In addition each calibration input is stored as a fixed input to a corresponding input node of the trained neural network. A multi-gas sensor output for at least part of the predefined number of gases to be detected and/or sensed is provided by the multi-gas sensor dependent on the trained neural network and actual measured sensor values from the sensor elements, which are provided to corresponding input nodes of the trained neural network.

The sensor elements are configured to provide a sensor signal. In the case where the sensor element is configured to detect a specific gas, the sensor signal of the sensor element is dependent on a kind of gas the senor element is exposed to. In the case where the sensor element is configured to sense a specific gas, the sensor signal of the sensor element is dependent on a concentration of the specific gas the sensor element is exposed to. In particular, the sensor signals comprise current values or voltage values. The sensor values of the sensor elements are representative for the provided sensor signals output by the sensor elements. The measurement results of the multi-gas sensor comprise all or part of the sensor values of the sensor elements of the multi-gas sensor.

By using production-relevant data, gas test data and a smart algorithm it is possible to reduce the necessary amount of tests for calibrating a multi-gas sensor. In this way a lot of time and therefore costs can be saved. By using additional neural inputs (calibration information input nodes), it is possible to use the same neural network for different sensors, even if they comprise small production fluctuations. Normally, the calibration information is constant over time, wherein the sensor values vary.

In an embodiment according to the first and second aspect, the trained neural network has learned during a preceding training phase how different sensor design data and/or different sensor production process parameters affect the sensor values of the sensor elements of the multi-gas sensor. Because of manufacturing tolerances it is not possible to produce exact copies of a gas sensor in a production process. There will always be small fluctuations in the provided output signals. This is the reason why nearly all gas sensor products need to be calibrated after assembly. Usually the small fluctuations have a certain reason, e.g., a small difference in the thickness of a gas sensitive layer. Alternatively or additionally a difference in the sintering temperature and therefore a difference in a grain size of a layer affect the sensor signals. By training the neural network with different sensor design data and/or different sensor production process parameters and/or exposing the multi-gas sensor to different physical stimuli (pressure, temperature or gas concentration) the neural network learns how the sensor values are affected by the different inputs.

In a further embodiment according to the first and second aspect, for the training of the neural network a neural network learning algorithm with a feed-forward propagation, a backward propagation and a gradient descent is used. This allows for providing a neural network which can be used to calculate the multi-sensor output signal sufficiently accurately for all gases the multi-gas sensor is configured to detect or sense, even if the multi-gas sensor is not tested for each gas to be detected or to be sensed by the multi-gas sensor.

In a further embodiment according to the first and second aspect, the neural network comprises at least two input nodes, at least tow output nodes and at least one hidden layer, wherein each hidden layer comprises two nodes or more than two nodes. In this way a sufficiently accurate multi-gas sensor output signal can be obtained while keeping the corresponding processing effort low.

In a further embodiment according to the first and second aspect, the calibration information comprises a thickness of the gas sensitive layer of at least one of the sensor elements, and/or a temperature during production, and/or a sheet thickness of at least one of the sensor elements, and/or a roughness of at least one of the sensor elements, and/or an average gas flow in a chemical vapour deposition, CVD, gas chamber, and/or an electrical resistance and/or capacitance and/or inductance of the metal layer of at least one of the sensor elements at various conditions, and/or sensor values of the multi-gas sensor provided when the multi-gas sensor is exposed to one of the gases to be detected and/or sensed by the multi-gas sensor, and/or sensor values of the multi-gas sensor provided when the multi-gas sensor is exposed to a gas mixture which comprises some or all of the gases to be detected and/or sensed by the multi-gas sensor, and/or other physical values provided by production or test equipment.

In a further embodiment, according to the first and second aspect, additional calibration information is provided which is included into hidden layer nodes. In this way the number of input nodes can be reduced.

Further embodiments are distinguished by a computer program, wherein the computer program is adjusted to perform the method according to the first aspect.

Other embodiments are distinguished by a computer program product comprising an executable program code, the program code executing the method according to the first aspect when executed by a data processing device.

The computer program product comprises in particular a medium readable by the data processing device on which the program code is stored.

The computer program may run on a central data processing device or a decentralised data processing device.

Yet other embodiments are distinguished by a multi-gas sensor. The multi-gas sensor comprises multiple sensor elements for different gases, wherein each sensor element is configured to provide a sensor value. Furthermore the multi-gas sensor comprises a processing unit configured to execute the above-mentioned computer program or comprises an apparatus according to the second aspect.

Optional embodiments of the first and second aspect shall apply here also to the further aspects.

BRIEF DESCRIPTION OF THE DRAWINGS

In the following, the present invention is described in detail with reference to the figures.

DETAILED DESCRIPTION OF ILLUSTRATIVE EMBODIMENTS

Figure 1:
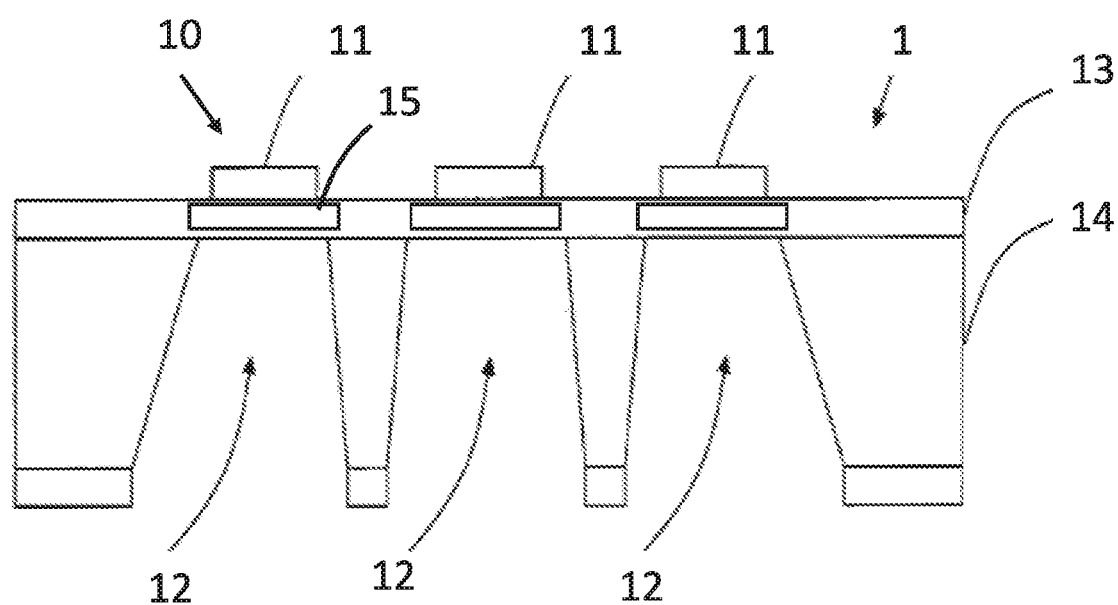
FIG. 1 shows a cross section of an exemplary gas sensor element.

FIG. 1 show a cross section of an exemplary multi-gas sensor 1. The multi-gas sensor 1 comprises multiple gas sensor elements 10. The multi-gas sensor 1 shown in FIG. 1, for example, comprises three sensor elements 10. The multi-gas sensor 1 is for example a semiconductor gas sensor.

Semiconductor gas sensors rely on a gas coming into contact with a metal oxide surface and then undergoing either oxidation or reduction. Absorption or desorption of the gas on the metal oxide changes either the conductivity or resistivity from a known baseline value. This change in conductivity or resistivity can be measured with electronic circuitry.

The metal oxide surface is usually a thin film of a transition or heavy metal. The exact metal that is used will depend on the application; examples of metals include tin dioxide ($SnO_2$) or tungsten oxide ($WO_3$). The film overlies a layer of silicon and is heated to a temperature between 200 and 400° C., again depending on the application. In this way, the chemical process is accelerated and the effects of fluctuating external temperatures are minimized.

The respective gas sensor element 10 shown in FIG. 1 comprises for example a sensing layer 11 of metal oxide. The gas sensor elements 10 are, for instance, integrated with a CMOS circuitry (not shown) on a single chip. A stack of layers 13 is arranged on a semiconductor substrate 14 required for the CMOS circuitry. The respective gas sensor element 10 comprises a membrane. A portion of the semiconductor substrate 14 is, for instance, etched away to form a cavity 12 at the location of the sensing layer 11. Remaining layers 13 and possibly a remaining portion of the substrate 14 form a thin membrane to support the layer 11.

The respective sensor element 10 comprises a heating element 15. The heating element 15 is embedded within the layer 13 and comprises conducting elements. The heating element 15 is configured to provide a local source of heat to heat the metal oxide layer 11 e.g., during operation of the gas sensor element 10. The temperature can rise rapidly around the metal oxide layer 11 on the membrane, while a thicker part of the gas sensor chip, i.e. the portion where the substrate 14 is not removed, reacts with a slower rise of temperature due to its thermal inertia. By controlling the heating element 15 accordingly, the metal oxide layer 11 can be activated for a measurement and be regenerated afterwards.

Each of the metal oxide layers 11 is contacted by two conductive electrodes and hence acts as a resistor. In the presence of a compound its resistance changes, thereby providing a measure of a concentration of the compound in the immediate vicinity of the metal oxide sensing layer 11. The change of the resistance and/or impedance can be measured by a voltage measurement.

Both the conductive electrodes and the heating element 15 are preferably connected to a control unit, which can be implemented as a part of the CMOS circuitry arranged on the same substrate 14.

Alternatively, a multi-gas sensor with other gas sensitive layers, for example, conducting polymers, can be used.

Gas sensors have to be calibrated. The output signals of the gas sensor elements 10 are generally in the form of a voltage value. Calibration is needed to implement a relation between the gas sensor element 10 signal and the concentration level of the corresponding gas.

Normally single-gas sensors are just calibrated to one certain gas. However, this bears the risk of undesired/unwanted cross sensitivities to other gases. For example, a single-gas sensor sold as an ethanol gas sensor usually is not only sensitive to ethanol, but instead it is also sensitive to acetone, for example. This means that if the sensor is exposed to e.g., 2 ppm of acetone, the sensor will give a signal of e.g., 1 ppm of ethanol. In many applications this cross sensitivity cannot be avoided and a suitable workaround has to be found.

There are also other applications for which a multi-gas sensor 1 is necessary, e.g., for quality inspection, medical applications but also for consumer applications. In particular for automated cooking a multi-gas sensor 1 is desirable which is configured to detect certain aromas of the cooked food.

Because of manufacturing tolerances it is not possible to produce exact copies of a gas sensor in a production process. There are always small fluctuations in the provided output signals. This is the reason why nearly all gas sensor products need to be calibrated after assembly. This means that calibration data is determined and used during operation of the gas sensor to adjust the sensor signals of the sensor elements 10 to provide accurate measurement output signals.

Figure 2:
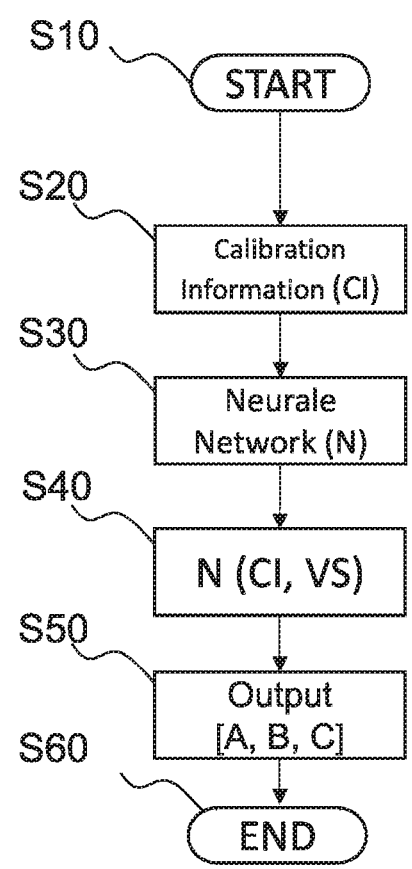
FIG. 2 shows a flow chart of an exemplary program to operate a multi-gas sensor.

FIG. 2 shows a flow chart of an exemplary program to operate a multi-gas sensor 1.

In a step S10 the program is started. In this step the program, in particular program parameters, is initialized.

In a step S20 at least one calibration input CI comprising sensor design data of the multi-gas sensor 1, which varies dependent on production process parameters, and/or sensor production process parameter data of the multi-gas sensor 1 and/or measurement results of the multi-gas sensor 1 captured when the multi-gas sensor 1 is exposed to one of the gases or a gas mixture to be detected and/or sensed by the multi-gas sensor 1 are provided.

For this, in a preceding phase, some gas exposure tests are performed and calibration information is gathered.

The calibration information comprises for instance: a thickness of the layer of at least one of the sensor elements 10, and/or a temperature during production, and/or a sheet thickness of at least one of the sensor elements 10, and/or a roughness of at least one of the sensor elements 10, and/or an average gas flow in a chemical vapour deposition, CVD, gas chamber, and/or an electrical resistance of the metal layer of at least one of the sensor elements 10 at various conditions, and/or sensor values VS of the multi-gas sensor 1 provided when the multi-gas sensor 1 is exposed to one of the gases to be detected and/or sensed by the multi-gas sensor 1, and/or sensor values VS of the multi-gas sensor 1 provided when the multi-gas sensor 1 is exposed to a gas mixture which comprises some or all of the gases to be detected and/or sensed by the multi-gas sensor 1.

In a step S30 a trained neural network N is provided, wherein the trained neural network N comprises an input layer with K input nodes, an output layer with L output nodes and at least one hidden layer.

The trained neural network N is used to correct the measured signals of the sensor elements 10 such that the multi-gas sensor 1 is configured to detect different gases and also a respective portion of each detected gas in a gas mixture, for example in an odor.

Embodiments provide relevant or most relevant calibration information and perform some gas exposure tests, i.e. not for all gases but only for some, and train the neural network N such that the neural network N can be used to provide the calibration also for other untested gases.

The input layer comprises multiple nodes, or neurons. The number of nodes of the input layer depends on the number of available input signals and input data. In the following the nodes of the input layer will be referred to as input nodes.

Figure 3:
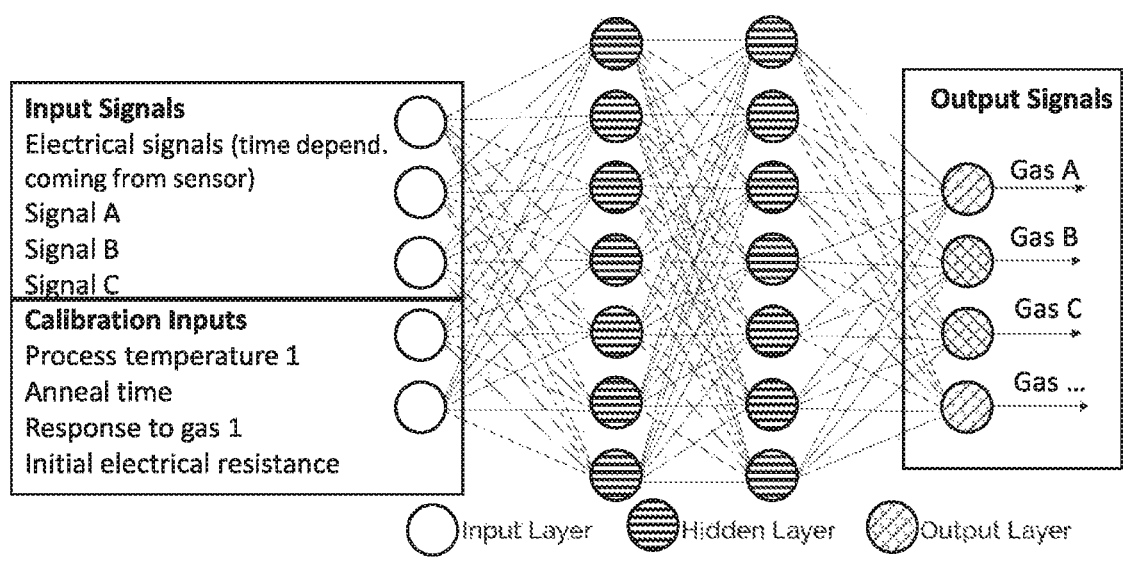
FIG. 3 shows an exemplary embodiment of the neural network.

An exemplary embodiment of the neural network N is shown in FIG. 3. The shown neural network N comprises at five input nodes, four output nodes and at least two hidden layers, wherein each hidden layer comprises seven nodes.

For achieving very good calibration results for a multi-gas sensor for at least four gases, for example, a neural network N comprises at least five input nodes, at least four output nodes and at least two hidden layers, wherein each hidden layer comprises 25 nodes or more than 25 nodes, can be used.

For example, the input layer comprises a given number A of nodes for the signals provided from the sensor elements 10 and a given number B of nodes for calibration inputs CI, wherein the sum of A and B is the number K of input nodes.

The output layer comprises L nodes, wherein, preferably the number L of nodes corresponds to the number M of gases to be detected or measured. For example, the output layer comprises one respective node for one specific gas. In the following the nodes of the output layer will be referred to as output nodes.

The neural network N comprises two hidden layers, for instance. Each hidden layer comprises multiples nodes, wherein the number of nodes in the different layers can be equal or different. In the following the nodes of the hidden layers will be referred to as internal nodes.

Each node of the input layer supplies a signal to each node of the hidden layer of the network adjacent to the input nodes. If the neural network N comprises more than one hidden layer, each internal node in the first layer, i.e., the hidden layer whose internal nodes receiving signals form the input nodes, generates a signal that is provided to each internal node of the second internal layer. Further hidden layers are connected to adjacent hidden layers in a similar manner. Each internal node in the hidden layer adjacent to the output layer provides a signal to each output unit. Each output node provides an output signal.

For the neural network N, the connections and/or the weight of connections are defined in a pre-phase, so that for a given input pattern the neural network N provides an appropriate output pattern.

For defining theses connections and weight of connections, respectively, the neural network N is "trained", wherein the weights of connections are adjusted using a form of feedback, on the basis of presented patterns and desired results. For the training of the neural network N, for instance a neural network learning algorithm with a feed-forward propagation, a backward propagation and a gradient descent is used.

In a step S40 each calibration input CI is stored as a fixed input to a corresponding input node of the trained neural network N.

In a step S50 a multi-gas sensor 1 output is provided for at least a part of the predefined number of gases to be detected and/or sensed by the multi-gas sensor 1 dependent on the trained neural network N and actual measured sensor values VS from the sensor elements 10, which are provided to corresponding input nodes of the trained neural network N.

In a step S60 the program ends.

In the following the working principle of the neural network N will be explained on the basis of a very simple multi-gas sensor 1. For example, the multi-gas sensor 1 is configured to detect three gases: methane, ethane and propane. These molecules are very similar. The only difference is the length of the molecule. It is well known that the sensitivity to larger molecules increases with increasing active layer thickness. As the neural network N has learned how the measured information, the increase of the active layer thickness and how the gas sensor responds to one gas, affects the sensor values VS, it is possible to calibrate the sensor to all three gases.

It is also possible, when knowing the gas response of methane and propane, to calculate the calibration of ethane.

Usually there are of course more than three gases, and the layer thickness is not the only parameter that is important for the sensor response, but this simplified example demonstrates the working principle. A neural network is very good at classifying problems. Usually the network is trained for a certain application and one sensor. By providing additional neuronal inputs (calibration inputs CI) it is possible to use the same neural network N for different sensors with, preferably, small production fluctuations.

It should be noted that some of the possible features and benefits of the invention are described herein with reference to different embodiments. A person skilled in the art recognizes that the features of the process and the device may be suitably combined, adapted or exchanged in order to arrive at further embodiments of the invention.

What is claimed is:

1. A method comprising:
    providing at least one calibration input comprising:
        sensor design data of a multi-gas sensor comprising multiple sensor elements, which varies dependent on production process parameters, wherein the multi-gas sensor is configured to detect and/or sense a predefined number M of different gases; and/or
        sensor production process parameter data of the multi-gas sensor; and/or
        measurement results of the multi-gas sensor captured when the multi-gas sensor is exposed to one of the gases or a gas mixture to be detected and/or sensed by the multi-gas sensor;
    providing a trained neural network comprising an input layer with K input nodes, an output layer with L output nodes and at least one hidden layer, wherein L, M and K are natural numbers;
    storing each calibration input as a fixed input to a corresponding input node of the trained neural network; and
    providing a multi-gas sensor output for at least a part of the gases to be detected and/or sensed by the multi-gas sensor dependent on the trained neural network and actual measured sensor values from the sensor elements, which are provided to corresponding input nodes of the trained neural network.

2. The method according to claim 1, wherein the trained neural network has learned during a preceding training phase how different sensor design data and/or different sensor manufacturing data affect the sensor values of the sensor elements of the multi-gas sensor.

3. The method according to claim 1, wherein, for a training of a neural network, a neural network learning algorithm with a feedforward propagation, a backward propagation and a gradient descent is used.

4. The method according to claim 1, wherein the trained neural network comprises at least two input nodes, at least two output nodes and at least one hidden layer, and wherein each hidden layer comprises two nodes or more than two nodes.

5. The method according to claim 1, wherein the calibration input comprises:
    a thickness of a gas sensitive layer of at least one of the sensor elements; and/or
    a temperature during production; and/or
    a sheet thickness of at least one of the sensor elements; and/or
    a roughness of at least one of the sensor elements; and/or
    an average gas flow in a chemical vapour deposition gas chamber; and/or
    an electrical resistance of a metal layer of at least one of the sensor elements at various conditions; and/or
    sensor values of the multi-gas sensor provided when the multi-gas sensor is exposed to one of the gases to be detected and/or sensed by the multi-gas sensor; and/or
    sensor values of the multi-gas sensor provided when the multi-gas sensor is exposed to a gas mixture which comprises some or all of the gases to be detected and/or sensed by the multi-gas sensor.

6. The method according to claim 1, wherein additional calibration information is provided which is included into hidden layer nodes.

7. An apparatus for operating a multi-gas sensor, wherein the apparatus is configured to execute the method according to claim 1.

8. A multi-gas sensor comprising:
    the multiple sensor elements for different gases, wherein each of the sensor elements is configured to provide a sensor value; and
    the apparatus according to claim 7.

* * * * *